United States Patent
Elfving et al.

(10) Patent No.: US 6,723,185 B1
(45) Date of Patent: Apr. 20, 2004

(54) METHOD FOR PRODUCING DEFECTS AND TENSILE RESIDUAL STRESSES

(75) Inventors: Kai Elfving, Kirjala (FI); Hannu Hanninen, TKK (FI); Mika Kemppainen, Kirkommuni (FI); Pekka Saarinen, Helsinki (FI); Iikka Virkkunen, Helsinki (FI)

(73) Assignee: Trueflaw Oy (FI)

( * ) Notice: Subject to any disclaimer, the term of this patent is extended or adjusted under 35 U.S.C. 154(b) by 0 days.

(21) Appl. No.: 09/856,008
(22) PCT Filed: Nov. 16, 1999
(86) PCT No.: PCT/FI99/00949
§ 371 (c)(1),
(2), (4) Date: Jul. 19, 2001
(87) PCT Pub. No.: WO00/29841
PCT Pub. Date: May 25, 2000

(30) Foreign Application Priority Data

Nov. 16, 1998 (FI) .................................................. 982471

(51) Int. Cl.$^7$ .............................. C21D 11/00; C21D 9/00
(52) U.S. Cl. ........................ 148/510; 148/508; 148/511; 148/639; 148/644
(58) Field of Search ................................. 148/508, 511, 148/510, 639, 644

(56) References Cited

U.S. PATENT DOCUMENTS

| | | |
|---|---|---|
| 4,108,647 A | * 8/1978 | Shaw .......................... 420/448 |
| 4,203,315 A | 5/1980 | Vieu et al. |
| 4,229,235 A | 10/1980 | Matsuda et al. |
| 4,704,892 A | 11/1987 | Tarnai |
| 4,729,235 A | 3/1988 | Podlech |
| 4,810,400 A | 3/1989 | Shinozaki et al. |
| 5,013,370 A | 5/1991 | Diaz |

FOREIGN PATENT DOCUMENTS

| | | | |
|---|---|---|---|
| JP | 410170421 A | * 6/1998 | ............ G01N/3/60 |
| WO | WO 98/19155 | 5/1998 | |

* cited by examiner

Primary Examiner—Deborah Yee
(74) Attorney, Agent, or Firm—Skinner and Associates

(57) ABSTRACT

A method, which is used to make controlled defects corresponding to natural flaws and residual stresses in various kinds of test pieces. Defects identical to natural flaws are required to qualify non-destructive testing (NDT) procedures. In the method, sequential, repeated, heating-cooling cycles are used to create defects and residual stresses. The shape of the heating and cooling pattern, the duration of the heating and cooling, and the number of thermal cycles are used to control the size of the defects and residual stresses obtained. The defect is grown without initial flaw or other nucleator. The defects correspond to natural flaws in terms of morphology and also of the signals obtained with NDT methods, and are suitable for use in, for example, NDT-qualification blocks.

6 Claims, 1 Drawing Sheet

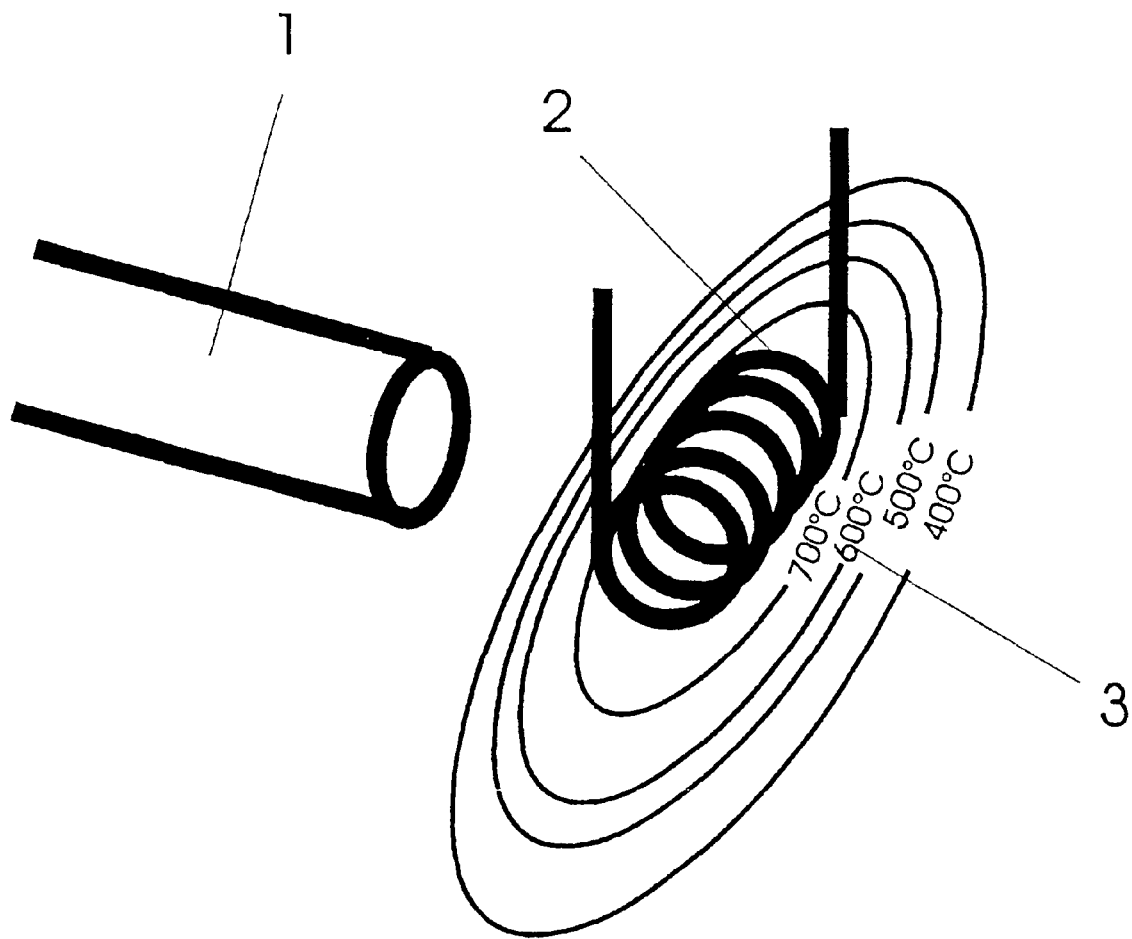

METHOD FOR PRODUCING DEFECTS AND TENSILE RESIDUAL STRESSES

The present invention relates to a method for producing controlled defects and residual stresses in test pieces.

Defects such as thermal fatigue cracks may appear in various components, e.g., in nuclear power plants, during operation. Non-destructive testing (NDT) procedures are used to examine pre defined valves, pipes, pipe connections, etc., during inspections carried out at regular intervals. In inspections carried out under field conditions, inaccuracies due to both the method and the personnel carrying them out always arise. Test pieces incorporating artificially created cracks similar to real ones are used to qualify NDT procedures and inspectors. The international PISC I, II, and III studies of the reliability of the non-destructive testing of materials, which have revealed obvious deficiencies in the detection and definition of defects, have demonstrated the need for qualification.

For example, qualification is required in the inspection of nuclear power plants. Instructions have been issued for the qualification of the NDT inspection of nuclear power plants (in the USA, ASME Code Section XI, in Europe, NRWG and ENIQ), according to which equipment, test pieces, procedures, and inspectors should be qualified.

According to the European qualification procedures, the dimensions (diameter, wall-thickness, etc.) of test pieces should correspond to the real objects being inspected. Similarly, the test pieces' other properties, such as material, shape, surface quality, method of manufacture, and location of welds must also correspond to those in actual plant components. The type, shape, size, location, orientation, and opening of the defects that occur must correspond closely enough to natural flaws The characteristics of the defects in qualification test pieces are highly significant to the entire qualification process. The use of test pieces with defects as similar as possible to natural defects will ensure that the inspection procedure in question can detect and define such defects with the required precision. Personnel-qualification tests determine if the inspector can detect and define the relevant defects with sufficient accuracy.

At present, methods are known for producing various kinds of cracks and defects in test pieces. In the known methods, an artificial crack is implanted to pieces usually by welding, a welding fault is made, or a notch is machined in the test piece. Japanese patent publication JP 57-034439 discloses a method that can be used to produce a crack in the surfacing of a plate-like piece. Another, also Japanese, patent publication JP 58-055752 discloses a method for making an artificial crack, in which a hole is machined in the surface of a joint between two pieces, after which the pieces are joined together. A third Japanese patent publication, JP 8-219953, discloses a method for manufacturing defects by machining grooves in a piece and filling them with a material with different acoustic properties to those of the parent material. No method is known for producing a defect in a piece of any shape at all, at any place at all, and of any desired orientation and shape. Producing cracks similar to natural ones is one of the central problems in qualification.

A method for producing a state of tensile residual stress is also known from U.S. Pat. No. 5,013,370, in which a tensile residual stress is induced in a test piece by cooling one surface of the piece and locally heating the opposite surface. The invention disclosed in the above publication requires the object or test piece being dealt with to have at least one stress-free portion, where a state of tensile residual stress can be induced. Heating is directed to this area and, if the tensile residual stress is to be produced in more than one area, the initial state of each of them must be stress-free.

In the publication referred to, opposite sides of the piece are heated and cooled. This arrangement induces an uncontrolled state of tensile stress in the area being treated. According to the patent in; question, a crack can be created in the induced field of tensile stress, e.g., by means of an aggressive crack-promoting environment, such as a boiling magnesium chloride solution, oxygenated water at a high temperature, etc.

Unlike the invention according to U.S. Pat. No. 5,013,370, the present invention can be used to create a wanted and controlled crack or a controlled residual stress state (either tensile or compressive), with no environmental or stress-state demands. As, in the present invention, the heating/cooling is not directed to different sides of the piece, there are no requirements concerning the size and shape of the piece. In addition, there are no requirements concerning the residual stress state in the test piece in its initial state.

The above and other advantages and benefits of the invention are achieved by means of a method, the characteristic features of which are described in the accompanying Claims.

The basic idea of the invention is to repeatedly alternately heat and cool the piece being treated, i.e. to fatigue it thermally, which will result in a crack identical to a natural flaws, or in a desired controlled state of residual stress.

In general, it can be stated that cracks induced by means of the methods disclosed in the above publications do not correspond to natural flaws, which is an obvious deficiency when manufacturing such test pieces for qualification. At present, cracks are produced in qualification test pieces either by welding separate pieces containing cracks into a test piece, or by welding a hot crack into a test piece, or simply by machining a notch in a test piece. Cracks implanted by welding may be natural and taken from actual pieces that have cracks in operation, or be artificially produced in separate test pieces. No matter how the crack being implanted has originated, the weld from the implanting will remain in the material. A hot crack is made by machining a narrow groove in the test piece and then by welding it shut using parameters that will cause the weld to crack in the desired direction. The welded joints in test pieces resulting from these methods can be easily detected by NDT inspection methods. Such aspects of machined notches as width and progression do not correspond to those of natural flaws.

The method now developed can be used to flexibly manufacture cracks similar to natural ones in any location in the test piece, irrespective of the shape or dimensions. The cracks are nucleated directly in the surface of the test piece. No crack initiator (machined notch etc.) is required. The cracks are grown in the surface of the test piece without the material experiencing micro-structural or other changes detectable by NDT methods. This is a significant advantage, because when transplanted or welded cracks are used, the inspector may notice the welded seams in the test piece and be alerted to make a more thorough search for cracks in the same area. Cracks created by the method that has been developed also correspond well to natural cracks, in terms such as the propagation and branching of the crack and the radius of the crack tip, all of which affect, for instance, the signals received in ultrasonic inspection and their interpretation.

The method now developed is based on the phenomenon of thermal fatigue and a new application of it. The phenomenon of thermal fatigue as such has been known for a long time, particularly for materials used at high temperatures.

The rapid cycling of heating and cooling in thermal fatigue causes steep temperature gradients to fluctuate in the test piece, resulting in stress and strain cycling that depend on the coefficient of thermal expansion of the material, and finally leading to fatigue damage.

Cracks manufactured using the method now developed are suitable for use in test pieces used to qualify NDT procedures. The cracks can be manufactured according to the following requirements:

- the morphology of the crack corresponds sufficiently to a natural crack for the response to it, when inspected by an NDT procedure, to be similar to that to a genuine crack
- the method can be used to manufacture individual cracks and networks of cracks
- the orientations of individual cracks can be varied
- cracks can be made in different sizes and shapes, unaffected by the thickness of the material of the piece
- if it is not intended to destruct the test pieces after the qualification test, the size of the cracks to be manufactured can be evaluated either during the fatigue cycling or on the basis of the fatigue parameters
- the heating and cooling patterns can be altered to make the cracks grow in desired directions.

BRIEF DESCRIPTION OF DRAWINGS

In the following, the operation of the invention is described with reference to the accompanying drawing, which show the heating and cooling arrangements. In the FIGURE, forced cooling (either liquid or gas cooling) is marked with the number 1, heating with the number 2, and the heating pattern (isotherms) with the number 3.

The arrangement according to the figure operates so that heater 2 is used to heat the surface to the desired temperature, after which the surface is cooled 1 to a lower temperature. During heating, a heating pattern 3, which is dependent on the heating output and time, arises, the shape of the pattern influencing the orientation of the defects created.

The operation of the invention is described with the aid of the following examples.

EXAMPLE 1.

A single crack, or several individual parallel cracks, was to be created in a pipe that corresponded to those used in a nuclear power plant. The heating pattern was shaped with its longer dimension circumferential to the pipe. This caused the cracks to grow in the pipe's axial direction. The heating and cooling cycles both lasted for 30 s. During the test, the maximum temperature was approximately 700° C. and the minimum temperature approximately 10° C. Forced cooling was used to prevent the heating pattern from spreading by thermal conduction. In forced cooling, cooling water is continuously directed to both sides of the heated area, also during the heating cycle.

The total number of cycles was 6500, both heating and cooling being included in a single cycle. At this number of cycles, three axially-oriented cracks grew from micro-cracks nucleated in the test piece.

The method according to the invention was used to form a single crack or multiple cracks in the parent material.

EXAMPLE 2.

The method was used to manufacture a crack or multiple cracks in a welded seam in a pipe. The cracks were manufactured in the inner surface of the pipe.

The heating pattern was shaped in such a way that it extended over the root pass of the weld, with its centre point close to the root pass. During calibration, a temperature of 700° C. was achieved when a heating time of 6 s was used. The cooling time was 10 s. A total of 17 803 cycles were made during the test. Penetrant testing was performed, demonstrating that cracks had formed on both sides of the weld. Besides the aforementioned cracks, a single crack, not extending over the root pass, had grown transversely to the weld.

The method can be used to manufacture cracks with properties corresponding to those of natural flaws, and which thus can be used in qualification test pieces. The method can be used to grow both a network of cracks specific to thermal fatigue and single cracks. Ultrasonic inspections of the manufactured cracks showed that the cracks' challenge to inspection procedures corresponded to reality.

The method has been used in the manner described in the above examples. In addition, the method can also be applied to produce residual stresses in a test piece. Residual stresses are also produced by thermally cycling on a desired area in a test piece, when permanent residual stress state will arise in the test piece. The changes of the residual stress- state during the cycling depend on the heating and cooling parameters used.

It should be noted that the invention is in no way restricted to the above disclosure or examples, but can be varied within the scope of the following claims and the stated inventive idea.

What is claimed is:

1. A method for producing artificial defects and/or residual stresses in test pieces, characterized by the steps of alternately heating and cooling the test object, on the same side of the test object, to create the defects and/or residual stresses.

2. A method according to claim 1, characterized by forming a shape of heating and/or cooling patterns whereby the defects and/or residual stresses are created.

3. A method according to claim 2, characterized in that the shape of the heating pattern is controlled by cooling the test piece outside the area of the desired pattern.

4. A method according to claim 1, characterized by sequentially repeating, a sufficient number of times, alternate heating and cooling cycles to achieve thermal fatigue damage.

5. A method according to claim 1, characterized by growing the defect without an initial flaw or other nucleator.

6. A method according to claim 1, characterized by controlling, by means of the heating and cooling output, the duration of the heating and cooling, and the number of thermal cycles, whereby the size of the manufactured defects and residual stresses is controlled.

* * * * *